United States Patent [19]

Hodgson

[11] Patent Number: 5,052,404
[45] Date of Patent: Oct. 1, 1991

[54] TORQUE TRANSMITTER

[75] Inventor: William S. Hodgson, Cohasset, Mass.

[73] Assignee: The MicroSpring Company, Inc., Norwell, Mass.

[21] Appl. No.: 569,133

[22] Filed: Aug. 17, 1990

Related U.S. Application Data

[63] Continuation of Ser. No. 318,628, Mar. 2, 1989, abandoned.

[51] Int. Cl.$^5$ .............................................. A61B 5/00
[52] U.S. Cl. .................................. 128/772; 74/502.5; 267/155; 267/168; 464/58
[58] Field of Search ................. 128/657, 772; 604/95, 604/164, 170, 280, 282; 15/104.33; 74/500.5, 502.4, 502.5, 502.6; 464/58, 60; 267/155, 168; 138/130, 134

[56] References Cited

U.S. PATENT DOCUMENTS

| Re. 25,543 | 3/1964 | Ruegg et al. | 464/58 |
| 177,490 | 5/1976 | Fones et al. | 464/58 |
| 1,170,196 | 2/1916 | Gallagher, Jr. | 267/168 |
| 1,905,197 | 4/1933 | Webb | 464/58 |

Primary Examiner—Randy Citrin Shay
Attorney, Agent, or Firm—Hale and Dorr

[57] ABSTRACT

A torque transmitter includes three coaxial helically wound springs of different inner and outer diameters positioned relative to each other such that the inner and outer generally circumferential surface of the center spring form interference fits with, respectively, the outer generally circumferential surface of the inner spring and the inner generally circumferential surface of the outer spring. The inner and outer springs are wrapped in one direction and the center spring is wrapped in the opposite direction.

12 Claims, 2 Drawing Sheets

TORQUE TRANSMITTER

This is a continuation of co-pending application Ser. No. 07/318,628 filed on Mar. 2, 1989, now abandoned.

FIELD OF INVENTION

This invention relates to torque transmitters and, more particularly, to hollow, flexible, small diameter devices for use in medical applications.

BACKGROUND OF INVENTION

There are in the art a number of flexible guide wires used in medical applications such as introducing catheters into human cardiovascular systems. Exemplary such devices are shown in U.S. Pat. Nos. 3,789,841, 4,538,622 and 4,545,390, which are hereby incorporated by reference. As discussed in these prior patents, in one typical application, such guide wires are introduced into a patient's femoral or brachial artery and are advanced through the artery into the coronary region, and the guide wire is manipulated to steer the device selectively into deeper and smaller coronary arteries. These prior art devices have a number of limitations. The wires tend to "set" when curved into the tortuous configuration required to follow along the artery and, particularly when curved, will not transmit torque/rotation from end-to-end on a substantially one-to-one basis.

The art also teaches a number of flexible power transmission shafts and couplings. See, e.g., U.S. Pat. Nos. 177,490, 779,374, 1,481,078, 1,678,335, 2,573,361, 3,628,352, 4,112,708, and U.S. Pat. No. Re. 25,543. These devices are, because among other things of their size, not useful in medical cardiovascular devices. Moreover, their design and construction is typically such that substantially one-to-one rotational torque transmission is neither necessary nor desired. In the flexible coupling of U.S. Pat. No. Re. 25,543, the circumference and inner surfaces of the individual springs are either ground to size or otherwise calibrated in order to telescope the individual layers into each other with a tight fit.

SUMMARY OF INVENTION

The present invention provides a small diameter device that has substantially the same one-to-one rotational torque transmission characteristics as a solid rod not only when straight but also when in a highly tortuous configuration, and that also is hollow so that a wire or the like can be fed through it.

The invention features a torque transmission device comprising three helically wound wire layers. The inner and outer layer are wrapped in the opposite helical directions from the central layer, and there is an interference fit between the inner and outer circumferential surfaces of the center layer and, respectively, the inner and outer layers when no torque is being applied to the device, i.e., the individual springs are constructed such that, standing alone and relaxed, the inner diameter of the central spring is less than the outer diameter of the inner spring and the outer diameter of the central spring is greater than the inner diameter of the outer spring. In preferred embodiments each layer comprises helically wrapped flat wire, and the inner and outer diameters of adjacent layers are such that, as compared to their non-overlapping state, there is a radial interference of not less than about 0.001 inch.

In addition to being able to transmit rotation/torque (either clockwise or counterclockwise) on an essentially one-to-one basis, the torque transmitter of the present invention has numerous other advantages. It is able to undergo tortuous bendings without kinking or setting, is resistant to longitudinal stretching and penetration, has high torsional stiffness, and is easily made watertight.

DRAWINGS

Figure 3:
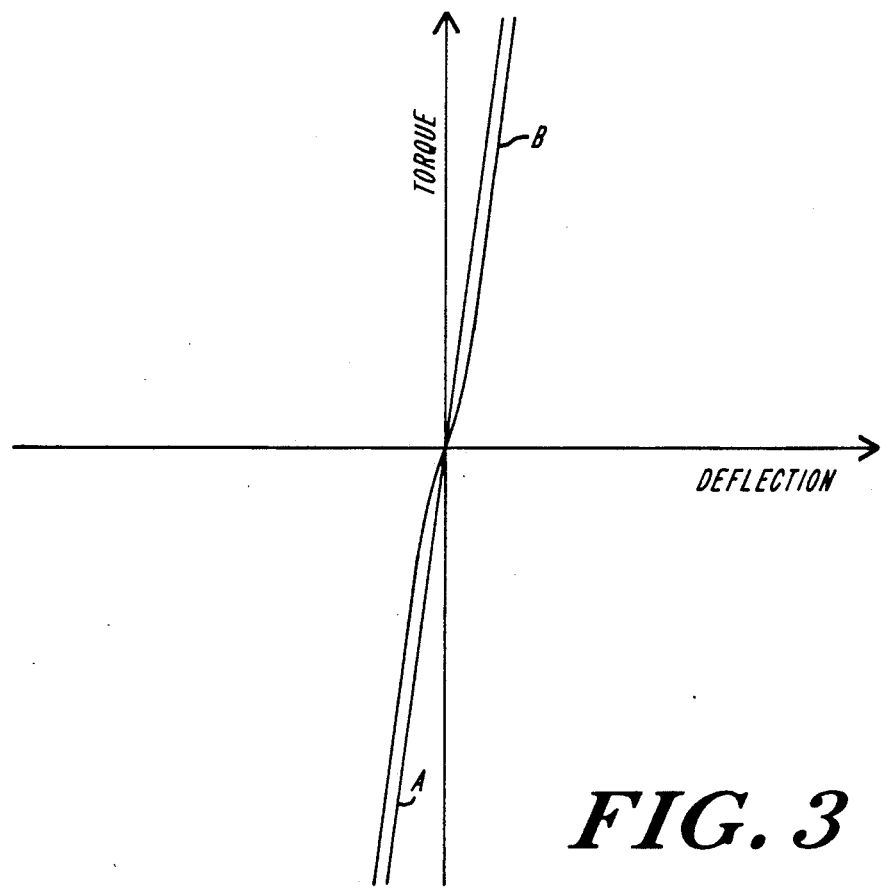

FIG. 3 schematically compares the torque transmitting characteristics of the present invention with those of a rigid rod.

Figure 1:
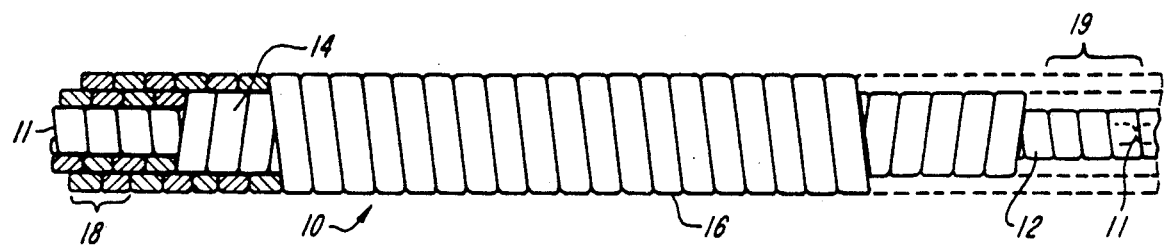
FIG. 1 shows, partially cut-away, a torque transmitter of the present invention in which each layer is single strand wire.
Figure 4:
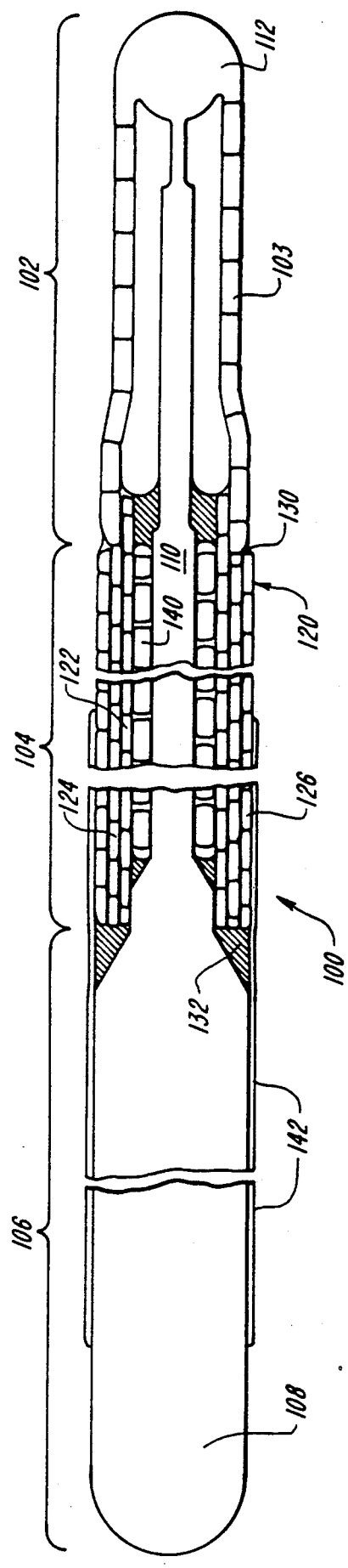

FIG. 4 shows in longitudinal section a medical guide wire assembly including the torque transmitter of FIG. 1.

DESCRIPTION OF PREFERRED EMBODIMENTS

Reference is now made to FIG. 1 which disclose a torque transmitter, generally designated 10, embodying the present invention. As shown, transmitter 10 comprises three helically wrapped wire springs 12, 14, 16.

As shown, the three springs are coaxial. Central spring 14 surrounds and engages the outer surface of inner spring 12, and itself is surrounded and engaged by the inner surface of outer spring 16. The outer diameter of device 10 is (for reasons discussed hereinafter with reference to FIG. 4) about 0.0128 in.; and this results in its inner diameter being about 0.0067 in.

Each of springs 12, 14, 16 is wrapped from a single strand of 304V stainless steel, diamond drawn flat wire. In the illustrated embodiment all the wire strands are 0.00080 in. thick (measured radially of the spring) and 0.003 in. wide (measured generally axially of the spring), and each spring is wrapped at helix angle of about 7° with the side edges of adjacent wire turns abutting each other. In transmitter 10, springs 12 and 16 are right hand wrapped (clockwise as viewed from either end), and spring 14 is left-hand wrapped (counterclockwise as viewed from either end). In practice, the coils of each spring are not precisely axially aligned.

In actual practice, the coils of each spring are not wound precisely flat to its longitudinal axis. Rather than being exactly coaxial to its axis and of precisely the same diameter, the coils may vary slightly in diameter and be slightly offset axially from each other. The result is that the outer diameter of each spring is greater than the inner diameter by an amount greater than twice the radial thickness of the wire strands from which the spring is wound.

For example, the outer diameter of each of springs 12, 14, 16 is somewhat more than 0.0016 in. greater than the inner diameter, (i.e., is more than twice the 0.00080 in. thickness of the wire forming the spring). Typically, the coil diameter variation and coil-to-coil misalignment is such that the difference between the overall inner and outer diameters of each spring in the device 10 is about 0.002 rather than 0.0016 in. Thus, in the assembled transmitter 10, the average diameter of the generally cylindrical interface between inner spring 12 and center spring 14 is about 0.0085 in., and the diameter of the interface between center spring 14 and outer spring 16 is about 0.0105 in. At each of the opposite ends 18, 19 of device 10, the ends of the three springs are brazed or soldered together, preferably leaving center bore 11 open, and the remaining portions of the springs engage but are relatively movable against each other.

Inner spring 12 initially is wrapped so that, in a relaxed condition and unconfined by any other spring, its inner diameter is about 0.0076 in. and its outer diameter is about 0.0092–0.0096 in. According to the preferred practice of the present invention, center layer spring 14 initially is wrapped to the same size. The outer layer spring 16 is wrapped so that its unconfined and relaxed inner and outer diameters are about 0.0089 in. and 0.0105–0.0109 in. respectively, i.e., are about the same as that of the center spring 14 in the complete device.

Thus, it will be evident that when the springs are relaxed and out of contact with each other, the inner diameter of center spring 14 is less than the outer diameter of inner spring 12, while the center spring's outer diameter is greater than the inner diameter of outer spring 16. This coupled with the fact that the inner and outer diameters of the overall device are, respectively, less and greater than the relaxed inner diameter of spring 12 and the relaxed outer diameter of spring 16, insures that, when the three springs are wrapped one around the other as shown in FIG. 1, there is an interference fit between center spring 14 and inner and outer springs 12 and 16. The outer surface of inner spring 12 presses tightly against the inner surface of center spring 14, since the relaxed outer diameter of inner spring 12 is greater than the inner diameter of center spring 14 and the inner spring 12 must be reduced in diameter from its relaxed configuration to fit into the center spring. Similarly, the inner surface of outer spring 16 presses tightly against the outer surface of center spring 14, since the relaxed inner diameter of outer spring 16 is less than the outer diameter of center spring 14 and the outer spring 16 must be expanded in diameter from its relaxed configuration to fit the center spring.

The exact relative inner and outer diameters of the spring may vary. Whatever the relative diameters, however, it is important that there be an interference fit between center spring 14 and the inner and outer springs 12, 16.

Figure 2:
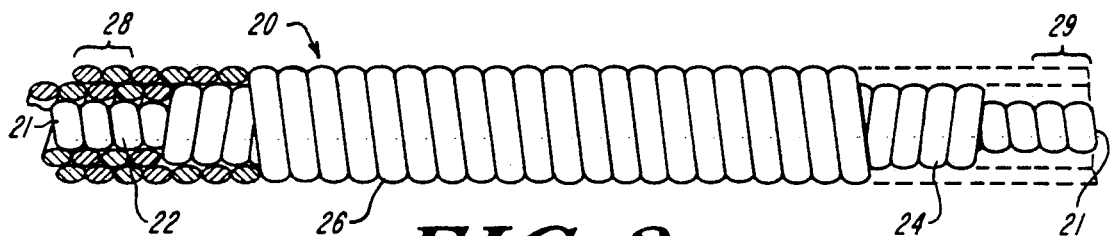
FIG. 2 shows, partially cut-away, a torque transmitter in which each layer is multi-strand.

FIG. 2 illustrates a second three-layer device, generally designated 20, embodying the present invention. The device 20 of FIG. 2 is similar to device 10 of FIG. 1 in that it comprises three coaxial helically-wrapped multi-strand (as illustrated, double strand) springs, designated 22, 24, 26 respectively. Center spring 24 surrounds inner spring 22 with the facing circumferential surfaces of the two engaging (i.e., providing an interference fit with) each other, while the outer surface of center spring 24 is surrounded by, and forms an interference fit with the inner surface of outer spring 26. As in the device 10 of FIG. 1, the inner and outer springs 22, 26 are helically wrapped in one direction (right-hand wrap, as shown) while the center spring 24 is wrapped in the other direction (as shown, a left-hand wrap). In all three springs, the helix angle is about the same, e.g., about 7°. The end portions 28, 29 of the springs are brazed together.

In device 10, each of the springs was wrapped from a single strand of flat wire. The springs 22, 24, 26 of device 20 are wrapped from double strands of round wire. Each round wire strand has a diameter of about 0.0015 in., and the strands are placed side-by-side and the springs wrapped so that each double-strand turn, measured axially of the spring is about 0.003 in. wide. When relaxed and unconfined, springs 22 and 24 each have an inner diameter of about 0.010 in. and an outer diameter of about 0.013 in. The inner and outer diameter of outer springs 26, when relaxed and unconfined, are about 0.013 and 0.016, respectively. The overall inner and outer diameters of device 20, with the three springs wrapped totally coaxially about each other, are about 0.009 in. and 0.018 in., respectively. It will thus be noted that, in device 20, inner spring 22 is reduced about 0.001 in diameter from its relaxed state, while center spring 24 and outer spring 26 each are increased about 0.002 in diameter.

The central conduit 21 through transmitter 20 is essentially watertight. Polymeric films are provided at the interface between springs 22 and 24 and that between spring 24 and 26, typically by applying a thin layer of liquid polymer during assembly and thereafter permitting it to cure.

Although the devices 10, 20 shown are rather short, e.g., the overall length is only a few times the diameter, in actual use the devices typically will have a length that is more than one hundred and often as much as a thousand times its diameter, e.g., a typical device will be about a foot long and about 0.0120 in. to about 0.060 in. in diameter.

In many applications, it is desirable that if one end of the device is rotated a specific number of degrees the other end will rotate the same amount, i.e., that there will be one-to-one rotation even under load, and even when the device is following a tortuous path.

In practice, perfect one-to-one rotation is impossible to achieve; under load there will always be some torsional deflection particularly as the device becomes very long relative to its diameter. The closest one-to-one rotation obtainable in the past, at least in relatively straight devices, has been that provided by a solid rod. Theoretical one-to-one transmission means that, regardless of the applied torque, there will be no relative rotational difference between the two ends of a device. Since even a solid rod is not infinitely stiff (i.e., will not have an infinitive modulus of elasticity), there will always be some relative deflection. The straight line A in FIG. 3 illustrates the relative deflection with torque of a typical solid rod; with a stiffer material, the line would be more nearly vertical. The deflection versus torque characteristics of devices of the present invention is shown by line B. As will be seen, such torque transmitters closely approximate solid rod characteristics; and unlike a solid rod the transmitter of the present invention will produce such linear and near one-to-one torsional stiffness even when bent through tight curves. The interference fit between the three springs of devices 10, 20 ensures that, no matter which direction the device is rotated, there will be an immediate response at the far end.

In one method of manufacture of device 10, center spring 14 is first placed over and around spring 12 so that there is an interference fit between the two. In practice this is accomplished as follows. Both the inner and center springs are placed on a 0.0065 in. mandrel, i.e., on a mandrel having an outer diameter that is less than the inner diameter of inner spring 12 (typically by an amount about equal to or slightly greater than the thickness of the wire forming the inner spring) in axial alignment with the adjacent ends of the two springs spaced a short distance from each other. The mandrel is rotated about its axis in the rotational direction such that, if the end of inner spring 12 farthest from central spring 14 is held fixed, against rotation, the inner spring 12 can be wrapped down onto the mandrel if the other end rotates in the same direction as the mandrel. The turns of spring 12 are then progressively (i.e., from the fixed and non-rotating end towards the end nearer spring 14) pressed against the mandrel (i.e., the spring is wiped down onto the mandrel, starting at the fixed end. The inner spring thus wrapped down tight on the mandrel along its length, slightly increasing the overall length of the inner spring 12 while reducing its outer diameter of about 0.0081 in. (0.0065 in. plus twice the spring's 0.00080 in. wire thickness). Then, with the mandrel still rotating in the same direction, the adjacent ends of the tightly wrapped inner spring 12 and the still essentially unrestrained center spring 14 are butted together, with the far end of center spring being held so that it will not rotate.

As should be evident, the frictional contact between the ends of inner spring 12 and center spring 14 tends (since the springs are wrapped in opposite directions) to open up center spring 14 (i.e., to increase its inner and outer diameter) while keeping inner spring 12 wrapped down on the mandrel; and the two springs are pushed axially towards each other, slipping center spring 14 over inner spring 12. The far ends of the two springs are then released, permitting inner spring 12 to try to expand (open-up) in diameter while center spring 14 simultaneously tends to contract (i.e., to close down), forming an interference fit between the two.

The same general procedure is used to fit outer spring 16 over the assembled inner and central spring unit. The just-assembled inner-central spring unit and the outer spring 16 are placed in spaced-apart axial alignment on a mandrel, typically having a diameter of about 0.0063 in., with their adjacent ends spaced slightly apart.

The direction of rotation of the mandrel is then reversed from that used in assembling the inner-central spring unit, i.e., the mandrel is rotated such that, if the end of the inner-central spring unit farthest from outer spring 16 is held fixed against rotation, the central spring 14 will tend to be wrapped down onto the inner spring 12 when the inner-central spring unit is pressed against (and thus tends to rotate in the same direction as) the mandrel. The central spring 14 is then progressively wiped down on the inner spring 12, starting at the fixed end. With the mandrel still rotating, the far end of the outer spring 16 then is held so it will not rotate, and the outer spring is moved axially so that its other end is butted against the inner-central spring unit. The frictional contact between the ends tends to open up outer spring 16, while keeping central spring 14 wrapped down against the inner spring 12, and the outer spring 16 is slipped over the inner-central spring unit. When the springs are released, the outer spring 16 contracts, forming the desired interference fit between it and central spring 14.

Reference is now made to FIG. 4 which shows a guide wire assembly, generally designated 100, which can be steered along and into very narrow blood vessels in cardiovascular surgical procedures. As shown, the guide wire assembly 100 may be used with balloon dilatation catheters of the general type described in U.S. Pat. No. 4,195,637 and in aforementioned U.S. Pat. No. 4,545,390. Such catheters are well-known in the art and are not part of the present invention.

An entire guide wire assembly of the type shown in FIG. 4 is often six or more feet long, and guide wire 100 has an overall diameter of less than about 0.014 in. It will thus be appreciated that although FIG. 5 is generally to scale, diametrically, the scale along the length of the wire assembly is very different from that shown.

As illustrated, guide wire assembly 100 includes a distal tip portion 102 about one inch long, an intermediate portion 104 about one foot long at the proximal end of tip portion 102, and a main guide wire portion 106 extending some five feet from the proximal end of the intermediate portion 104. The solid main guide wire 108 includes an approximately constant diameter portion about five feet long and 0.013 in. in diameter forming the main guide wire portion 108 of assembly 100 and a distal portion 110 of reduced diameter extending coaxially through intermediate portion 104 and terminating in a flat portion which is secured (typically by welding) at its distal end to the essentially hemispherical tip 112 of tip portion 102. It will be seen that the distal portion 110 of guide wire 108 acts as a safety wire for the tip and intermediate portions of the guide wire assembly.

Tip portion 102 comprises a tapered spring 103 of helically wrapped platinum wire (about 0.0015–0.0016 in. thick by 0.003 to 0.004 in. wide) having a diameter of about 0.013 in. at its proximal end (where it is brazed to intermediate portion 104) and a diameter of 0.010 in. at its distal end (where it is welded to tip 112).

Intermediate portion 104 includes a torque transmitter 120 (essentially identical to device 10 of FIG. 1) including a right hand inner spring 122, a left hand central spring 124 and a right hand outer spring 126 wrapped around each other so that there are interference fits between the outside circumference of central spring 124 and the inner circumference of outer spring 126, and between the inner circumference of central spring 124 and the outer circumference of inner spring 122. As previously discussed, the adjacent spring layers are not connected to each other except at their opposite ends where they are brazed, both to each other and, respectively, to the tip and main guide wire portions 102, 106. The braze areas, each of which have an overall length of about 0.05 in., are indicated by shading and identified by the reference numbers 130, 132.

A tantalum (or, alternatively, gold, tungsten or platinum) marker wire spring 140 is fitted over the reduced diameter portion 110 of guide wire within intermediate portion 104. The purpose of marker wire spring 140 is to provide a good fluoroscope image to a physician using guide wire assembly 100, and there is only a loose fit between the marker wire spring 140 and guide wire portion 110 and between spring 140 and torque transmitter 120.

A thin, e.g., 0.0005 in. thick, urethane film layer 142 is spray deposited on the outer surface of main wire 108 from a point about two inches from the wire's proximal end to and over the braze area 132 where it is connected to intermediate portion 104. As will be evident, film 142 increases the overall diameter of the guide wire assembly by about 0.001. If, therefore, it is desirable that the overall diameter of the particular assembly not exceed 0.014 in., the overall diameter of the guide wire 108 and of the torque transmitter 120 should not exceed 0.013 in. or, to provide for manufacturing tolerances, 0.0128 in.

OTHER EMBODIMENTS

In such other embodiments, by way of example, the ends of the three springs forming the torque transmitter may no be brazed together or otherwise fixed to each other, and the springs themselves may be what is known in the field as an "open wind" in which the adjacent coils are not abutting.

Similarly one or two of the springs may be wound from single strand wire while the other springs are multiple (e.g., 2 to 6) strand windings; and different spring also be made from different cross-section (e.g., rectangular, square, round) wire.

Typically, the outer diameter of the overall torque transmitter will be less than about 0.060 in., and preferably less than about 0.030 in.; and the wire from which the individual springs are wound will have a thickness (measured radially of the wound spring) of less than 0.007 in., and preferably in the range of 0.0005 to 0.003 in.

As used in the claims, the term "interference fit" between any two adjacent spring layers of an assembled device means that the inner diameter of the outer layer is less than the outer diameter of the inner layer when the two layers are separated and no torque is being applied to either. By way of example, there is in the device 10 of FIG. 1, there is an "interference fit" between the outer spring 16 and the center spring 14 because, when the outer spring 16 is separated from the inner-center spring unit (e.g., before the two are assembled) the inner diameter of the outer opening is less than the outer diameter of the inner-center spring unit (and in the illustrated embodiment is less also than the outer diameter of the center spring 14 above). There also is an "interference fit" between the center spring 14 and the inner spring 12 because, when the two springs are separated as before they are assembled, inner spring 12 has an outer diameter greater than the inner diameter of center spring 14.

What is claimed is:

1. A torque transmitter including three coaxial helically wound springs, an inner spring, a center spring, and an outer spring, said springs having different inner and outer diameters and being positioned relative to each other such that said inner spring is surrounded by said center spring and said center spring is in turn surrounded by said outer spring, and said inner and said outer springs being wrapped in one direction and said center spring being wrapped in the opposite direction, said torque transmitter being characterized in that:

the inner generally circumferential surface of said center spring forms an interference fit with the outer generally circumferential surface of said inner spring; and, the outer generally circumferential surface of said center spring forms an interference fit with the inner generally circumferential surface of said outer spring.

2. The torque transmitter of claim 1 wherein end portions of said inner, center and outer springs are adjacent and are fixed against rotation relative to each other and portions of said springs intermediate said end portions are moveable relative to each other.

3. The torque transmitter of claim 1 wherein each of said springs is wrapped from generally flat wire.

4. The torque transmitter of claim 1 wherein at least one of said springs is wrapped from a multiple wire strand.

5. The torque transmitter of claim 1 wherein the diameter of the generally circumferential outer surface of said outer spring is not more than about 0.060 in.

6. The torque transmitter of claim 5 wherein said diameter is not more than about 0.030 in.

7. The torque transmitter of claim 1 wherein the length of said transmitter is not less than about 100 times the diameter of the generally circumferential outer surface of said outer spring.

8. The torque transmitter of claim 7 wherein said length is not less than about 500 times said diameter.

9. The torque transmitter of claim 1 wherein each of said springs is wrapped from wire having a thickness less than about 0.007 in., said thickness being measured radially of said torque transmitter.

10. The torque transmitter of claim 9 wherein said thickness or diameter is in the range of 0.0005 to 0.003 in.

11. The torque transmitter of claim 1 wherein the inner surface of said inner coil defines a generally cylindrical hollow cavity, the generally cylindrical surface of said outer spring has a diameter of not more than about 0.060 in., the length of said transmitter is not less than about 100 times the diameter of said generally circumferential outer surface of said outer spring, and each of said springs is wrapped from wire having a diameter less than about 0.007 in.

12. A medical guide wire assembly comprising:
the torque transmitter of claim 1; and,
a main portion connected to said torque transmitter and generally axially aligned therewith, said main portion extending from a point proximal to the end of said torque transmitter.

* * * * *